United States Patent

Murata et al.

[11] Patent Number: 5,053,544
[45] Date of Patent: Oct. 1, 1991

[54] DIAMINO COMPOUND AND ITS INTERMEDIATES

[75] Inventors: Shizuo Murata; Minoru Nakayama, both of Ichiharashi, Japan

[73] Assignee: Chisso Corporation, Osaka, Japan

[21] Appl. No.: 631,448

[22] Filed: Dec. 21, 1990

[30] Foreign Application Priority Data

Jan. 25, 1990 [JP] Japan .................................. 1-15746

[51] Int. Cl.$^5$ ............................................ C07C 217/14
[52] U.S. Cl. ............................. 564/430; 528/125; 528/126; 528/128; 568/717; 568/931
[58] Field of Search ............... 564/430; 528/125, 126; 350/349

[56] References Cited

U.S. PATENT DOCUMENTS

| | | | |
|---|---|---|---|
| 3,247,199 | 2/1966 | Marxer | 564/325 |
| 3,705,870 | 12/1972 | Darmory et al. | 564/430 |
| 3,817,921 | 6/1974 | Brode et al. | 564/430 |
| 4,239,880 | 12/1980 | Darms | 564/430 |
| 4,864,008 | 9/1989 | Murata et al. | 528/125 |

FOREIGN PATENT DOCUMENTS

| | | | |
|---|---|---|---|
| 184751A | 12/1984 | European Pat. Off. | 564/430 |
| 61-240223 | 10/1986 | Japan . | |
| 62-004252A | 10/1987 | Japan | 564/430 |
| 64-62616 | 3/1989 | Japan . | |

OTHER PUBLICATIONS

Korshak et al, "Cardo Polymer", Reviews in Macromolecular Chemistry, 12, 1974/1975 pp. 100-129.

Primary Examiner—Glennon H. Hollrah
Assistant Examiner—Shailendra Kumar
Attorney, Agent, or Firm—Leydig Voit & Mayer

[57] ABSTRACT

A novel diamino compound and a dinitro compound and a diol compound as its derivatives are provided, which diamino compound is useful as a raw material for polyimide compounds for an aligning film in a liquid crystal display element exhibiting a high pretilt angle, and expressed by the formula

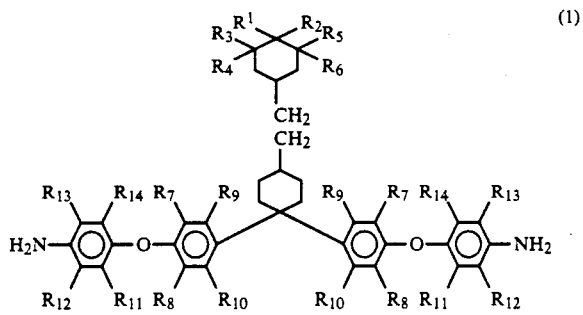

wherein $R_1$ to $R_6$ each are H or 1-22C alkyl and may be the same as or different from one another, and $R_7$ to $R_{14}$ each are H or 1-3C alkyl and may be the same as or different from one another.

4 Claims, No Drawings

DIAMINO COMPOUND AND ITS INTERMEDIATES

BACKGROUND OF THE INVENTION

1. Field of the Invention

This invention relates to a novel diamino compound and its derivatives. More particularly it relates to a novel diamino compound useful as a raw material for preparing a polyimide which may be employed as an aligning film in a liquid crystal display element exhibiting a high pretilt angle, and to a dinitro compound which may be used and a diol compound as intermediates of the above diamino compound.

2. Description of the Related Art

As to liquid crystal display elements used for watches, electronic calculators, etc., a twisted nematic (hereinafter abbreviated to TN) mode exhibiting a structure having the aligning direction of nematic liquid crystal molecules twisted by 90° between a pair of upper and lower electrode substrates, has now been employed as a main current. However, as to this display mode, when it is applied to a high duty drive, the contrast is inferior and the angle of view is narrow; hence it has been unsatisfactory for improving the display quality and the display surface. Recently, a liquid crystal display device making use of a super-twisted birefringence effect has been announced (T.J. Scheffer and J. Nethring, Appl. Phys. Lett., 45 (10), 1021 (1984)). Since then, a liquid crystal display element making use of a supertwisted nematic mode (hereinafter abbreviated to STN) having the aligning direction of nematic liquid crystal molecules twisted by 180° to 300° between the upper and lower electrode substrates has been developed; thus even in the case of a liquid crystal display element affording a large pictorial surface, those having a satisfactory display quality have come to be obtained. In the case of an aligning film used for such elements, it is necessary to afford a definite angle (hereinafter abbreviated to pretilt angle) between the substrate planes and the liquid crystal molecules, in order to not only align the liquid crystal molecules, but also to improve response properties and ensure the bistability. Further it is preferred that the larger the twist angle, the larger the pretilt angle. Among these elements, in the case of those having a relatively small twist angle (180° to 200° twist), the interface treatment on the electrode substrates is sufficient with a cell provided with an aligning film having an interface of a currently generally employed pretilt angle (abbreviated to $\theta$) of 5° or less. However, in the case of those elements using a mode having a twist angle of 200° to 300° wherein they exhibit a better display quality, it is necessary to use an interface of a higher pretilt angle ($5° < \theta \leq 30°$); thus a liquid crystal display cell provided with an aligning film satisfying such a pretilt angle is necessary.

In the case of currently used aligning films of polyamides for a TN mode, display cells prepared on the commercial scale have a pretilt angle limited to 5°.

Polyimide aligning films having a high pretilt angle for a STN mode are also existent, but they still have a problem in the aspect of the stability and reproducibility of a pretilt angle over the total region of the cell substrates having a broad display area. In order to obtain a high pretilt angle with certainty, a thin film formation of $SiO_2$, etc. by means of oblique vacuum deposition is the best method among those currently carried out. However, such a thin film formation by means of vacuum deposition, when carried out by commercial mass production, is disadvantageous because of the cost of its preparation apparatus. Thus, it has been earnestly desired to obtain an alignment and a high pretilt angle by means of an interface treatment by rubbing a thin film of an organic substance according to the same method as employed in a conventional TN mode to thereby realize the stability and reproducibility of the pretilt angle.

Japanese patent application laid-open No. Sho 61-240223 discloses a liquid crystal display element provided with a liquid crystal aligning film using a polyimide resin having a repetitive unit expressed by the formula

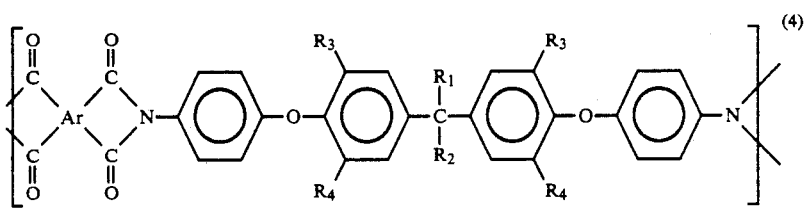

Further, as a raw material for the unit, a concrete example of a diamine expressed by the formula

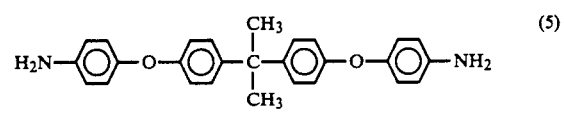

is disclosed therein.

However, the polyimide aligning film obtained using this diamino compound has a drawback that no high pretilt angle is obtained as illustrated in Comparative example mentioned later. Thus, a novel diamino compound used as a raw material for organic aligning films has been desired.

SUMMARY OF THE INVENTION

The object of the present invention is to solve the above problems and provide a novel diamino compound as a raw material for an aligning film of organic substances capable of realizing superior aligning properties and a uniform and high pretilt angle by a rubbing treatment, and intermediates of the diamino compound.

The present invention in a first aspect resides in a diamino compound expressed by the formula

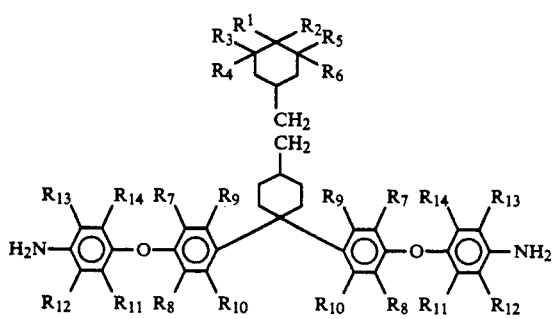

The present invention in a second aspect resides in a dinitro compound expressed by the formula

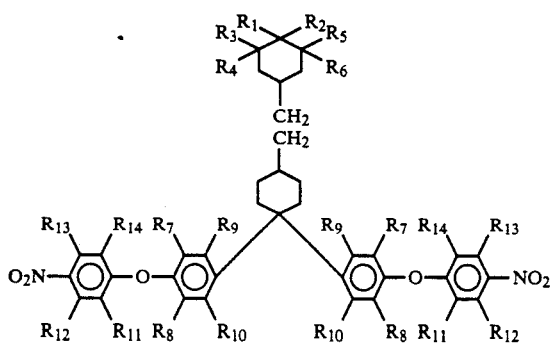

The present invention in a third aspect resides in a diol compound expressed by the formula

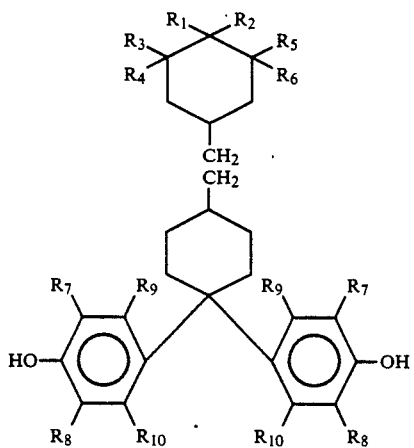

In the above formulas (1), (2) and (3), $R_1$ to $R_6$ each represent a hydrogen atom or an alkyl group of 1 to 22 carbon atoms, and may be the same as or partly or totally different from one another, and $R_7$ to $R_{14}$ each represent a hydrogen atom or an alkyl group of 1 to 3 carbon atoms, and may be the same as or partly or totally different from one another.

DETAILED DESCRIPTION OF PREFERRED EMBODIMENTS

Concrete examples of the diamino compound of the present invention are as follows:

1,1-bis[4-(4-aminophenoxy)phenyl]-4-(2-cyclohexylethyl)cyclohexane
1,1-bis[4-(4-aminophenoxy)phenyl]-4-[2-(trans-4-methylcyclohexyl)ethyl]cyclohexane
1,1-bis[4-(4-aminophenoxy)phenyl]-4-[2-(trans-4-ethylcyclohexyl)ethyl]cyclohexane
1,1-bis[4-(4-aminophenoxy)phenyl]-4-[2-(trans-4-n-propylcyclohexyl)ethyl]cyclohexane
1-bis[4-(4-aminophenoxy)phenyl]-4-[2-(trans-4-n-butylcyclohexyl)ethyl]cyclohexane
1,1-bis[4-(4-aminophenoxy)phenyl]-4-[2-(trans-4-n-pentylcyclohexyl)ethyl]cyclohexane
1,1-bis[4-(4-aminophenoxy)phenyl]-4-[2-(trans-4-n-hexylcyclohexyl)ethyl]cyclohexane
1,1-bis[4-(4-aminophenoxy)phenyl]-4-[2-(trans-4-n-heptylcyclohexyl)ethyl]cyclohexane
1,1-bis[4-(4-aminophenoxy)phenyl]-4-[2-(trans-4-n-octylcyclohexyl)ethyl]cyclohexane
1,1-bis[4-(4-aminophenoxy)phenyl]-4-[2-(trans-4-n-nonylcyclohexyl)ethyl]cyclohexane
1,1-bis[4-(4-aminophenoxy)phenyl]-4-[2-(trans-4-n-decylcyclohexyl)ethyl]cyclohexane
1,1-bis[4-(4-aminophenoxy)phenyl]-4-[2-(trans-4-n-undecylcyclohexyl)ethyl]cyclohexane
1,1-bis[4-(4-aminophenoxy)phenyl]-4-[2-(trans-4-n-dodecylcyclohexyl)ethyl]cyclohexane
1,1-bis[4-(4-aminophenoxy)phenyl]-4-[2-(trans-4-n-tridecylcyclohexyl)ethyl]cyclohexane
1,1-bis[4-(4-aminophenoxy)phenyl]-4-[2-(trans-4-n-tetradecylcyclohexyl)ethyl]cyclohexane
1,1-bis[4-(4-aminophenoxy)phenyl]-4-[2-(trans-4-n-pentadecylcyclohexyl)ethyl]cyclohexane
1,1-bis[4-(4-aminophenoxy)phenyl]-4-[2-(trans-4-n-hexadecylcyclohexyl)ethyl]cyclohexane
1,1-bis[4-(4-aminophenoxy)phenyl]-4-[2-(trans-4-n-heptadecylcyclohexyl)ethyl]cyclohexane
1,1-bis[4-(4-aminophenoxy)phenyl]-4-[2-(trans-4-n-octadecylcyclohexyl)ethyl]cyclohexane
1,1-bis[4-(4-aminophenoxy)phenyl]-4-[2-(trans-4-n-nonadecylcyclohexyl)ethyl]cyclohexane Concrete examples of the dinitro compound of the present invention are as follows:

1,1-bis[4-(4-nitrophenoxy)phenyl]-4-(2-cyclohexylethyl)cyclohexane
1,1-bis[4-(4-nitrophenoxy)phenyl]-4-[2-(trans-4-methylcyclohexyl)ethyl]cyclohexane
1,1-bis[4-(4-nitrophenoxy)phenyl]-4-[2-(trans-4ethylcyclohexyl)ethyl]cyclohexane
1,1-bis[4-(4-nitrophenoxy)phenyl]-4-[2-(trans-4-n-propylcyclohexyl)ethyl]cyclohexane
1,1-bis[4-(4-nitrophenoxy)phenyl]-4-[2-(trans-4-n-butylcyclohexyl)ethyl]cyclohexane
1,1-bis[4-(4-nitrophenoxy)phenyl]-4-[2-(trans-4-n-pentylcyclohexyl)ethyl]cyclohexane
1,1-bis[4-(4-nitrophenoxy)phenyl]-4-[2-(trans-4-n-hexylcyclohexyl)ethyl]cyclohexane
1,1-bis[4-(4-nitrophenoxy)phenyl]-4-[2-(trans-4-n-heptylcyclohexyl)ethyl]cyclohexane
1,1-bis[4-(4-nitrophenoxy)phenyl]-4-[2-(trans-4-n-octylcyclohexyl)ethyl]cyclohexane
1,1-bis[4-(4-nitrophenoxy)phenyl]-4-[2-(trans-4-n-nonylcyclohexyl)ethyl]cyclohexane
1,1-bis[4-(4-nitrophenoxy)phenyl]-4-[2-(trans-4-n-decylcyclohexyl)ethyl]cyclohexane
1,1-bis[4-(4-nitrophenoxy)phenyl]-4-[2-(trans-4-n-undecylcyclohexyl)ethyl]cyclohexane
1,1-bis[4-(4-nitrophenoxy)phenyl]-4-[2-(trans-4-n-dodecylcyclohexyl)ethyl]cyclohexane
1,1-bis[4-(4-nitrophenoxy)phenyl]-4-[2-(trans-4-n-tridecylcyclohexyl)ethyl]cyclohexane
1,1-bis[4-(4-nitrophenoxy)phenyl]-4-[2-(trans-4-n-tetradecylcyclohexyl)ethyl]cyclohexane 1,1-bis[4-(4-nitrophenoxy)phenyl]-4-[2-(trans-4-n-pentadecylcyclohexyl)ethyl]cyclohexane
1,1-bis[4-(4-nitrophenoxy)phenyl]-4-[2-(trans-4-n-hexadecylcyclohexyl)ethyl]cyclohexane
1,1-bis[4-(4-nitrophenoxy)phenyl]-4-[2-(trans-4-n-heptadecylcyclohexyl)ethyl]cyclohexane
1,1-bis[4-(4-nitrophenoxy)phenyl]-4-[2-(trans-4-n-octadecylcyclohexyl)ethyl]cyclohexane
1,1-bis[4-(4-nitrophenoxy)phenyl]-4-[2-(trans-4-n-nonadecylcyclohexyl)ethyl]cyclohexane Concrete examples of the diol compound of the present invention are as follows:

1,1-bis(4-hydroxyphenyl)-4-(2-cyclohexylethyl)cyclohexane
1,1-bis(4-hydroxyphenyl)-4-[2-(trans-4-methylcyclohexyl)ethyl]cyclohexane
1,1-bis(4-hydroxyphenyl)-4-[2-(trans-4-ethylcyclohexyl)ethyl]cyclohexane
1,1-bis(4-hydroxyphenyl)-4-[2-(trans-4-n-propylcyclohexyl)ethyl]cyclohexane
1,1-bis(4-hydroxyphenyl)-4-[2-(trans-4-n-butylcyclohexyl)ethyl]cyclohexane
1,1-bis(4-hydroxyphenyl)-4-[2-(trans-4-n-pentylcyclohexyl)ethyl]cyclohexane
1,1-bis(4-hydroxyphenyl)-4-[2-(trans-4-n-hexylcyclohexyl)ethyl]cyclohexane
1,1-bis(4-hydroxyphenyl)-4-[2-(trans-4-n-heptylcyclohexyl)ethyl]cyclohexane
1,1-bis(4-hydroxyphenyl)-4-[2-(trans-4-n-octylcyclohexyl)ethyl]cyclohexane
1,1-bis(4-hydroxyphenyl)-4-[2-(trans-4-n-nonylcyclohexyl)ethyl]cyclohexane
1,1-bis(4-hydroxyphenyl)-4-[2-(trans-4-n-decylcyclohexyl)ethyl]cyclohexane
1,1-bis(4-hydroxyphenyl)-4-[2-(trans-4-n-undecylcyclohexyl)ethyl]cyclohexane
1,1-bis(4-hydroxyphenyl)-4-[2-(trans-4-n-dodecylchclohexyl)ethyl]cyclohexane
1,1-bis(4-hydroxyphenyl)-4-[2-(trans-4-n-tridecylchclohexyl)ethyl]cyclohexane
1,1-bis(4-hydroxyphenyl)-4-[2-(trans-4-n-tetradecylcyclohexyl)ethyl]cyclohexane
1,1-bis(4-hydroxyphenyl)-4-[2-(trans-4-n-pentadecylcyclohexyl)ethyl]cyclohexane
1,1-bis(4-hydroxyphenyl)-4-[2-(trans-4-n-hexadecylcyclohexyl)ethyl]cyclohexane
1,1-bis(4-hydroxyphenyl)-4-[2-(trans-4-n-heptadecylcyclohexyl)ethyl]cyclohexane
1,1-bis(4-hydroxyphenyl)-4-[2-(trans-4-n-octadecylcyclohexyl)ethyl]cyclohexane
1,1-bis(4-hydroxyphenyl)-4-[2-(trans-4-n-nonadecylcyclohexyl)ethyl]cyclohexane The diamino compound (1) of the present invention may be prepared according to the following steps, and the diol compound (3) of the present invention and the dinitro compound (2) are each an intermediate of the compound (1):

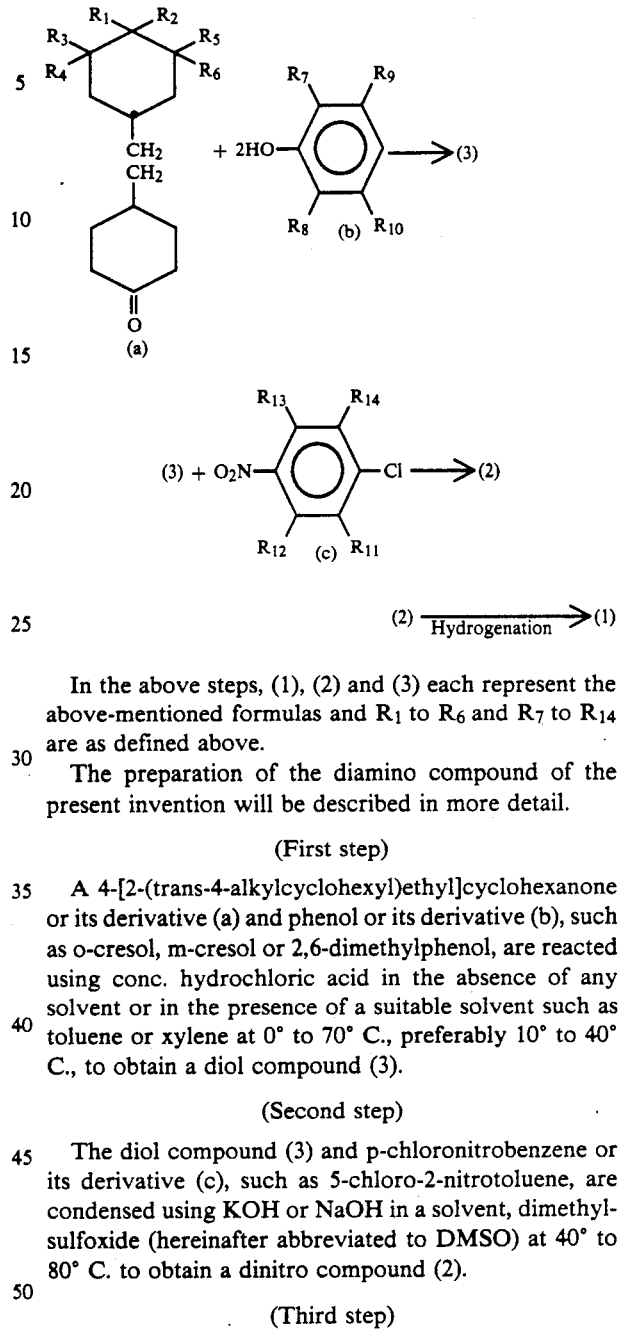

In the above steps, (1), (2) and (3) each represent the above-mentioned formulas and $R_1$ to $R_6$ and $R_7$ to $R_{14}$ are as defined above.

The preparation of the diamino compound of the present invention will be described in more detail.

(First step)

A 4-[2-(trans-4-alkylcyclohexyl)ethyl]cyclohexanone or its derivative (a) and phenol or its derivative (b), such as o-cresol, m-cresol or 2,6-dimethylphenol, are reacted using conc. hydrochloric acid in the absence of any solvent or in the presence of a suitable solvent such as toluene or xylene at 0° to 70° C., preferably 10° to 40° C., to obtain a diol compound (3).

(Second step)

The diol compound (3) and p-chloronitrobenzene or its derivative (c), such as 5-chloro-2-nitrotoluene, are condensed using KOH or NaOH in a solvent, dimethylsulfoxide (hereinafter abbreviated to DMSO) at 40° to 80° C. to obtain a dinitro compound (2).

(Third step)

The dinitro compound (2) is subjected to catalytic hydrogenation using a catalyst, palladium-carbon (hereinafter abbreviated to Pd-C) in a solvent such as toluene, xylene, benzene, ethanol or methanol at 30° to 80° C. to obtain a diamino compound (1).

As shown in the above reaction steps it is possible to prepare various diol compounds by suitably choosing $R_1$ to $R_6$ and $R_7$ to $R_{10}$ in the first step and also to prepare various dinitro compounds and diamino compounds by suitably choosing $R_{11}$ to $R_{14}$ in the second step. (Example)

The preparation of the compounds of the present invention will be illustrated in more detail and also the application results of the resulting polyimide resins to liquid crystal aligning films will be illustrated.

EXAMPLE 1

(First step)

4-[2-(Trans-4-n-pentylcyclohexyl)ethyl]cyclohexanone (112.4 g), phenol (152.7 g) and calcium chloride (90.1 g) were mixed, followed by gradually dropwise adding conc. hydrochloric acid (68 ml) with vigorous stirring at room temperature, agitating the mixture for 30 minutes after completion of the dropwise addition, further allowing the resulting material to stand at room temperature for 24 hours, adding hot water (0.5 l) and ethyl acetate (2 l) to dissolve it on heating, washing with saturated NaCl aqueous solution using hot water at 40° to 50° C., drying over $Na_2SO_4$, filtering, concentrating and recrystallizing the resulting concentrate from a mixed solvent of ethyl alcohol and methyl alcohol (87:13) (SOLMIX ® made by Nihon Kasei Co., Ltd.) to obtain white crystals of 1,1-bis(4-hydroxyphenyl)-4-[2-(trans-4-n-pentylcyclohexyl)ethyl]cyclohexane (78.8 g) as a diol compound of the present invention. M.P.: 203.4–204.4° C.

(Second step)

To 1,1-bis(4-hydroxyphenyl)-4-[2-(trans-4-n-pentylcyclohexyl)ethyl]cyclohexane (48.8 g) obtained at the first step were added DMSO (300 ml) and KOH (14.7 g), followed by dissolving the mixture on heating at 65° C., dropwise adding a solution of p-chloronitrobenzene (30.8 g) in DMSO (100 ml) at 65° C. to react with the mixture, aging the resulting material for 5 hours, cooling down to room temperature after completion of the reaction, extracting with dichloromethane, washing with 1N-HCl, then washing with 1N-NaOH aqueous solution, further washing with saturated NaCl aqueous solution till the washing solution became neutral, drying over $MgSO_4$, subjecting to alumina column treatment, distilling off the eluate, and recrystallizing the resulting concentrate from toluene solvent to obtain pale yellow crystals of 1,1-bis[4-(4-nitrophenoxy)-phenyl]-4-[2-trans-4-n-pentylcyclohexyl)ethyl]cyclohexane (57.0 g) as a dinitro compound of the present invention. M.P.: 160.5°–163.0° C.

(Third step)

1,1-Bis[4-(4-nitrophenoxy)phenyl]-4-[2-(trans-4-npentylcyclohexyl)ethyl]cyclohexane (25.8 g) obtained at the second step was dissolved in a mixed solvent of toluene (200 ml) and SOLMIX (60 ml), followed by adding Pd-C catalyst (Pd content: 5% and water content: 55.9%) (1.5 g), cooling the mixture with water under the atmospheric pressure, contacting it with hydrogen gas with stirring, filtering off the catalyst after completion of the reaction, concentrating the resulting solution, and recrystallizing the concentrate with a mixed solvent of toluene and SOLMIX, to obtain 1,1-bis[4-(4-aminophenoxy)phenyl]-4-[2-(trans-4-n-pentylcyclohexyl)ethyl]cyclohexane (10.5 g) as a diamino compound of the present invention. M.P.: 170.7°–171.9° C.

EXAMPLE 2

Example 1 was repeated except that 4-[2-(trans-4-n-pentylcyclohexyl)ethyl]cyclohexanone in Example 1 was changed to 4-[2(trans-4-n-heptylcyclohexyl)ethyl]-cyclohexanone.

At the first step, white crystals of 1,1-bis(4-hydroxyphenyl)-4-[2-(trans-4-n-heptylcyclohexyl)ethyl]-cyclohexanone were obtained. M.P.: 188.7°–189.6° C.

At the second step, pale yellow crystals of 1,1-bis[4-(4-nitrophenoxy)phenyl]-4-[2-trans-4-n-heptylcyclohexyl)ethyl]cyclohexane were obtained. M.P.: 129.3°–130.3° C.

At the third step, pale brown crystals of a diamino compound, 1,1-bis[4-(4-aminophenoxy)pehnyl]-4-[2-(trans-4-n-heptylcyclohexyl)ethyl]cyclohexane was obtained. M.P.: 167.7°–168.3° C.

APPLICATION EXAMPLE 1

Into a 200 ml capacity, four-necked flask provided with a stirrer, a thermometer, a condenser and a nitrogen-purging means were fed dehydrated, purified N-methyl-2-pyrrolidone (60 ml) and then 1,1-bis[4-(4-aminophenoxy)phenyl]-4-[2-(trans-4-n-pentylcyclohexyl)ethyl]cyclohexane (10.43 g), followed by dissolving these with stirring, cooling the solution down to 13° C., at a time feeding pyromellitic dianhydride (4.12 g), reacting the mixture with stirring under cooling, adding p-aminophenyltrimethoxysilane (0.91 g) after one hour, reacting the mixture with stirring at 20° C. for one hour, and diluting the reaction solution with N-methyl-2-pyrrolidone (NMP) (75 ml) to obtain a 10% by weight transparent solution of a polyamic acid. This solution had a viscosity at 25° C. of 155 cps as measured at 25°±0.1° C. by an E type viscometer (made by Tokyo Keiki Co., Ltd.). The solution was diluted with a solution obtained by mixing butyl cellosolve with N-methyl-2-pyrrolidone (1:1), into a 3% by weight solution, followed by coating the solution on a transparent glass substrate provided with an ITO (indium oxide-tin oxide) transparent electrode on one side of the substrate, according to a revolution coating method (spinner method) under revolution conditions of 2,500 rpm and 20 seconds, drying the resulting substrate at 100° C. for 10 minutes, subjecting it to heat treatment at 200° C. for 90 minutes in an oven, to obtain a polyether imide film having a coating thickness of about 700 Å.

The coated surfaces of two substrates having the polyether imide film formed thereon were respectively subjected to rubbing treatment to obtain a liquid crystal aligning film, followed by setting up a liquid crystal cell of a cell thickness of 20 μm so that the two liquid crystal-aligning films might be parallel in the rubbing direction and opposed to each other, filling liquid crystals ZLI-1132 made by Merck Co., Ltd. in the cell, heating the resulting cell up to an isotropic liquid temperature and gradually cooling it to obtain a liquid crystal element. This element had superior aligning properties and exhibited a pretilt angle of 20° as calculated by measuring its electric capacity.

APPLICATION EXAMPLE 2

Application example 1 was repeated except that 1,1-bis[4-(4-aminophenoxy)phenyl]-4-[2-trans-4-n-pentylcyclohexyl)ethyl]cyclohexane in Application example 1 was replaced by 1,1-bis[4-(4-aminophenoxy)phenyl]-4[2-(trans-4-n-heptylcyclohexyl)ethyl]cyclohexane, to obtain a 10% by weight solution of a polyamic acid having a viscosity of 145 cps. This solution was diluted, coated and heat-treated in the same manners as in Application example 1 to obtain a polyether imide film of a film thickness of about 1,100 Å.

Two of the substrates each having the polyether imide film formed thereon were each made up into a substrate having a liquid crystal-aligning film in the same manner as in Application example 1, to obtain a liquid crystal element having a cell thickness of 20 μm. Liquid crystals ZLI-1132 made by Merck Co., Ltd. were placed in the liquid crystal element. The resulting cell exhibited superior aligning properties. The liquid crystal element had a pretilt angle of 15.3°.

COMPARATIVE APPLICATION EXAMPLE 2,2-Bis[4-(4-aminophenoxy)phenyl]propane (24.92 g), pyromellitic anhydride (15.16 g) and p-aminophenyltrimethoxysilane (3.36 g) were polymerized at 5° to 10° C. using N-methyl-2-pyrrolidone (380.3 ml) as solvent, to obtain a polyamic acid solution (10% by weight, $\eta_{20}=113$ cps), followed by diluting the solution with a mixed solvent of N-methyl-2-pyrrolidone (one part) and butyl cellosolve (one part), to a solution of 3% concentration, followed by coating according to a revolution coating method (spinner method) under coating conditions of 3,000 rpm for 20 seconds, preheating at 100° C. for 10 minutes, and heat-treating at 200° C. for one hour to obtain a polyether imide film having a film thickness of about 600 Å, further subjecting it to a rubbing treatment to set up a liquid crystal cell, which exhibited a pretilt angle of 5°.

As seen from the above results, when a 1,1-bis[4-(4-aminophenoxy)phenyl]-4-[2-(trans-4-alkylcyclohexyl)ethyl]cyclohexane is used as a raw material for aligning films, it is possible to obtain a high tilt angle. Further, when the length of the alkyl chain bonded to the cyclohexane in the raw materials is increased, it is possible to increase the tilt angle, and when a suitable alkyl chain length is chosen, it is possible to obtain an optimum pretilt angle necessary when liquid crystal elements are prepared.

(Effectiveness of the Invention)

The diamino compound of the present invention and the dinitro compound and the diol compound as its intermediates are novel compounds which were not heretofore known. Polyimide compounds prepared using the diamino compound as raw material make it possible to realize a high pretilt angle required for STN liquid crystal display elements, by conventional rubbing treatment. This is presumed to be brought about by the cyclohexane ring of the diamino compound as a raw material and the alkyl group bonded to the ring. While the diamino compound of the present invention having such a specific feature has been designed mainly as a raw material intermediate for organic aligning films for STN, the diamino compounds are usable as high-molecular compounds such as other polyimides, polyamides, etc. and for modifying them, and they are also usable for other purposes such as epoxy cross-linking materials, etc. and further it is possible to expect introduction of new specific features into high-molecular compounds.

What we claim is:

1. A diamino compound expressed by the formula

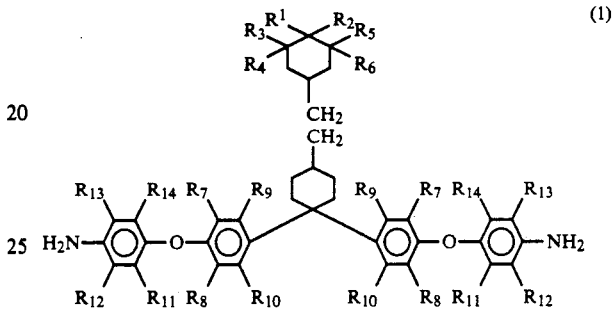

wherein $R_1$ to $R_6$ each represent a hydrogen atom or an alkyl group of 1 to 22 carbon atoms, and may be the same as or different from one another, and $R_7$ to $R_{14}$ each represent a hydrogen atom or an alkyl group of 1 to 3 carbon atoms, and may be the same as or different from one another.

2. A diamino compound according to claim 1 wherein $R_1$ represents a straight chain alkyl group having 1 to 19 carbon atoms and each of $R_2$ to $R_{14}$ represents a hydrogen atom.

3. A diamino compound according to claim 1 wherein $R_1$ represents a n-pentyl group and each of $R_2$ to $R_{14}$ represents a hydrogen atom.

4. A diamino compound according to claim 1 wherein $R_1$ represents a n-heptyl group and each of $R_2$ to $R_{14}$ represents a hydrogen atom.

* * * * *